(12) United States Patent
Ye et al.

(10) Patent No.: US 11,980,686 B1
(45) Date of Patent: May 14, 2024

(54) AGOMELATINE ORAL TRANSMUCOSAL FILM

(71) Applicant: Xiamen LP Pharmaceutical Co., Ltd., Xiamen (CN)

(72) Inventors: Ying Ye, Xiamen (CN); Haijian Zhu, Xiamen (CN); Rongbin Ling, Xiamen (CN); Zhoue Gao, Xiamen (CN); Avinash Singh, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 18/462,245

(22) Filed: Sep. 6, 2023

(30) Foreign Application Priority Data

Aug. 21, 2023 (CN) .......................... 202311054277.8

(51) Int. Cl.
*A61K 9/00* (2006.01)
*A61K 31/165* (2006.01)
*A61K 47/26* (2006.01)
*A61K 47/38* (2006.01)

(52) U.S. Cl.
CPC ............ *A61K 9/006* (2013.01); *A61K 31/165* (2013.01); *A61K 47/26* (2013.01); *A61K 47/38* (2013.01)

(58) Field of Classification Search
CPC ...... A61K 9/006; A61K 31/165; A61K 47/26; A61K 47/38
See application file for complete search history.

(56) References Cited

U.S. PATENT DOCUMENTS

2019/0110981 A1* 4/2019 Weimann .............. A61K 9/0014
2021/0186859 A1* 6/2021 Xie ........................ A61K 47/32
2022/0401389 A1* 12/2022 Mohr ..................... A61K 9/006

FOREIGN PATENT DOCUMENTS

CN 116211835 A 6/2023

OTHER PUBLICATIONS

Shinkar, D.M., et al., Development and Evaluation of Orally Fast Dissolving Film of Agomelatine, vol. 10 No. 10, pp. 497-505, Oct. 10, 2017, International Journal of ChemTech Research, Online.
Lavanya A., et. al., Formulation and in Vitro Evaluation of Fast Dissolving Sublingual Films of Agomelatine. Oct. 1, 2019, international Journal of Pharmacy and Biological Sciences-IJPBS, https://doi.org/10.21276/ijpbs.2019.9.4.26.
Taylor & Francis Online, Said, Mayada, et al., Transdermal Agomelatine Microemulsion Gel: Pyramidal Screening, Statistical Optimization and In Vivo Bioavailability, vol. 24, No. 1, pp. 1159-1169, Jan. 1, 2017, https://doi.org/10.1080/10717544.2017.1365392, Drug Delivery.

* cited by examiner

*Primary Examiner* — Doan T Phan
(74) *Attorney, Agent, or Firm* — Perkins Coie LLP; Viola Kung

(57) ABSTRACT

The present invention provides an oral transmucosal film for delivering agomelatine through the buccal mucosa or sublingual mucosa. The film is a bilayer structure containing a mucoadhesive layer with amorphous agomelatine and a water-soluble backing layer without agomelatine. The film has improved bioavailability and improved palatability. The mucoadhesive layer comprises comprising 0.1%-40% by weight of amorphous agomelatine, or a pharmaceutical acceptable salt thereof, 50-98% by weight of a first film-forming material, 0.5-20% by weight of an oil phase excipient, and 0.5-17% by weight of a surfactant. The backing layer comprises 60-100% (w/w) of one or more film-forming agents.

11 Claims, No Drawings

AGOMELATINE ORAL TRANSMUCOSAL FILM

This application claims the priority of Chinese Application No. 202311054277.8, filed Aug. 21, 2023; which is incorporated herein by reference in its entirety.

FIELD OF INVENTION

The present invention relates to an oral transmucosal film for delivering agomelatine through the buccal mucosa or sublingual mucosa.

BACKGROUND OF THE INVENTION

Agomelatine is the world's first melatonin receptor agonist antidepressant, which was developed and marketed by Les Laboratories Servier Industries in 2009. It is another blockbuster drug in the antipsychotic category. The drug is an agonist of melatonin receptor (MT1 and MT2) and an antagonist of 5-hydroxytryptamine 2C (5-HT2C) receptor, through the synergistic effect, it can synchronize the disordered biological rhythm of patients with depression to achieve the antidepressant activity. Agomelatine has a rapid onset of action, has antidepressant, antianxiety, sleeping disorder and biological clock regulation. It can improve the nighttime sleep without affecting the daytime biological rhythm. When compared with other antidepressant, agomelatine has fewer adverse reactions, higher safety, and no withdrawal reaction, thus agomelatine provides a new method for clinical treatment of major depressive disorder.

Agomelatine is currently available in the market as an immediate release tablet with strength of 25 mg. The product is clinically efficacious, but the tablet dosage has some disadvantages. First, because of high first-pass metabolism of agomelatine, the bioavailability of oral tablet is very low about less than 5%. The coefficient of variation of AUC of agomelatine is about 100%-150%, the inter-individual variation is 104%, and the intra-subject variation is 157%. Second, agomelatine has side effect of hepatotoxicity, which can lead to reversible increase of transaminase in some patients clinically; so liver function monitoring is required during clinical use.

Agomelatine tablets have low oral absorption, less bioavailability, large coefficient of variation of AUC (100%-150%), and hepatotoxicity. All patients should undergo liver function tests at the beginning and regular reexaminations during treatment. At the same time, it is recommended to conduct regular laboratory tests at 6 weeks of treatment (at the end of acute phase treatment), 12 weeks and 24 weeks (at the end of maintenance treatment). The existing problems have affected the clinical and patient drug safety.

There exists a need for a pharmaceutical composition for delivering agomelatine with improved bioavailability, a rapid effect and low hepatotoxicity.

DETAILED DESCRIPTION OF THE INVENTION

The inventors have discovered a pharmaceutical composition suitable for buccal or sublingual administration of agomelatine with improved bioavailability. The pharmaceutical composition is an oral transmucosal film. The agomelatine oral transmucosal film of the present invention adheres to the buccal or sublingual mucosa and disintegrates or dissolves by the saliva within a few minutes, and agomelatine is absorbed directly into the blood vessels via buccal or sublingual mucosa, which avoids gastrointestinal degradation and bypasses the liver first pass effect, and consequently the bioavailability of agomelatine is improved dramatically comparing with agomelatine oral tablets.

Buccal epithelium is a relatively permeable non-keratinized tissue; where blood vessels drain directly into the jugular vein. The oral transmucosal film of the present invention promotes the absorption of agomelatine, and provides high bioavailability of agomelatine. The oral transmucosal film of the present invention is designed to achieve a desired agomelatine absorption profile and peak blood level and to provide a favorable pharmacokinetic profile with a good bioavailability. The oral transmucosal film of the present invention is suitable for buccal or sublingual delivery of agomelatine with improved bioavailability as much as 8 to 51 times of the agomelatine oral tablets.

According to literature, agomelatine may have severe liver toxicity when administered orally, and liver function should be strictly tested during clinical use. The dosage of agomelatine oral tablets currently available in the market is 25 mg/day, which is a relatively large dosage and may cause certain damage to the liver function of a patient. Comparing with oral tablets available on the market, the agomelatine transmucosal film of the present invention achieves the same therapeutic effect with improved bioavailability and reduced risk of liver damage.

The active ingredient agomelatine in the present oral transmucosal film is in an amorphous form to increase the dissolution rate in buccal or sublingual administration. The amorphous agomelatine is rapidly released and absorbed, which provides a fast onset of action after administered.

Agomelatine has strong irritation to the tongue in the oral cavity. During oral administration, agomelatine diffuses into the oral cavity and irritates patient's tongue, which causes patient's compliance issue. The oral transmucosal film of the present invention is in a bilayer film having a mucoadhesive layer comprising agomelatine, and a backing layer that is drug free. The backing layer effectively prevents the drug in the mucoadhesive layer from diffusing to the oral cavity during oral administration and thus preventing a patient from feeling tongue irritation and thus improving the patient's compliance.

The oral transmucosal film of the present invention is administered buccally or sublingually by placing the pharmaceutical composition in the mouth of a subject, either under the tongue (sublingual) or between the gum and the cheek (buccal). Agomelatine is absorbed through the mucous membranes of the mouth to enter the bloodstream, which reduces the time to reach a peak plasma concentration ($T_{max}$), comparing to that of agomelatine oral tablets. Additionally, agomelatine in the present invention enters bloodstream through absorption so the administration is not affected by food.

The oral transmucosal agomelatine film of the present invention is in a bilayer film form comprising a mucoadhesive layer (a drug layer) and a backing layer. The mucoadhesive layer comprises about 0.1-40% by weight of agomelatine or a pharmaceutical acceptable salt thereof, in an amorphous state, about 50-98% by weight of a first film-forming material, 0.5-20% by weight of an oil phase excipient, and 0.5-17% by weight of a surfactant. Agomelatine is in an amorphous state in the mucoadhesive layer of the film.

"Pharmaceutically acceptable salts," as used herein, are salts that retain the desired biological activity of the parent compound and do not impart undesired toxicological effects.

"About" when used in this application, refers to ±10% of the recited value.

Unless otherwise specified, % used in this application refers to weight by weight %.

The active ingredient in the pharmaceutical composition is agomelatine or a pharmaceutically acceptable salt thereof, e.g., agomelatine iodine salts such as agomelatine hydriodide trihydrate, agomelatine hemitriiodide, agomelatine hemitriiodide iodine and agomelatine phosphate, agomelatine hydrogensulfate, agomelatine mesylate, and agomelatine besylate. The amount of agomelatine in the mucoadhesive layer is preferably 0.1-10 mg, preferably 0.1-5 mg, 0.3-10 mg, 0.3-5 mg, or 0.5-3 mg. The weight percentage of agomelatine in the drug layer in general is 0.1-40% w/w, preferably 0.5-30% or 0.5-25% w/w.

The film-forming materials useful in the mucoadhesive layer include one or more materials selected from the group consisting of: hypromellose (HPMC), hydroxypropyl cellulose (HPC), ethylene glycol and vinyl ethanol graft copolymer (PVA-PEG), polyvinyl alcohol (PVA), copovidone (PVP), and polyethylene oxide (PEO). The film-forming materials have good compatibility with agomelatine and provide the drug layer with a sufficiently high drug-loading capacity. The formed film has good mechanical properties and flexibility, and agomelatine is maintained in an amorphous state in the film for a long time without recrystallization or crystal conversion. The weight percentage of the film-forming materials in the drug layer in general is about 50-98% w/w, preferably 70-95%, w/w or 80-95% w/w.

The oil phase excipient is selected from the group consisting of: propylene glycol dicaprate, glyceryl monolinoleate, monoglyceride of oleic acid, diethylene glycol monoethyl ether, oleoyl polyoxyl-6 glycerides, propylene glycol monolaurate, polyglyceryl-4 oleate, capryl/capric acid triglycerides, polyoxyl 20 cetostearyl ether, polyglyceryl-3 diisostearate, polyoxyl 35 castor oil, and any combination thereof. The weight percentage of the oil phase excipient in the drug layer in general is about 0.5-25% w/w, preferably 1-20%, w/w or 1-15% w/w.

The surfactant is an ionic or a non-ionic surfactant selected from the group consisting of: lauroyl polyoxyl-32 glyceride, stearoyl polyoxyl-32 glyceride, oleic acid polyethylene glycol glyceride, linoleoyl polyoxyl-6 glyceride, sodium dodecyl sulfate, mono and di-glycerides of capryl/capric acid, polyoxyl-32 stearate, caprylocaproyl polyoxyl-8 glycerides, polyoxyl 15 hydroxy stearate and any combination thereof. The weight percentage of the surfactant in the drug layer in general is about 0.5-17% w/w, preferably 1-15%, w/w or 1-10% w/w.

The drug layer of the present agomelatine transmucosal film contains one or more oil phase excipients and surfactants (emulsifiers), which provide a self-emulsifying drug delivery system. A self-emulsifying drug delivery system in general is used for delivering a hydrophobic drug to improve the bioavailability of a water-insoluble drug. In a self-emulsifying drug delivery system, the drug spontaneously forms an emulsion under mild agitation in an aqueous phase. The agomelatine transmucosal film has good water solubility and the film can completely dissolve in water within 5 minutes to form microemulsions of agomelatine through self-emulsification. The agomelatine transmucosal film of the invention achieves good absorption curve, required peak blood concentration, and good bioavailability.

Bioavailability is affected by the rate of agomelatine absorbed through the oral mucosa and the time of the film adhering to the oral mucosa. The drug layer of the present oral transmucosal film provides good adherence of the film to the oral mucosa until the film is dissolved. In one embodiment, the agomelatine transmucosal film optionally further comprises one or more adhesives in the drug layer; the adhesive should improve adhesion and does not affect agomelatine dissolution or reduce agomelatine bioavailability. Adhesives suitable for the present invention include one or more materials such as hypromellose, hydroxypropyl cellulose, povidone, polyglutamic acid, polycarbophil, carbomer, dextran sulfate, and chondroitin sulfate, sodium CMC.

The backing layer is water-soluble and comprises a second film-forming material. The backing layer prevents agomelatine from diffusing into the oral cavity of a patient during oral administration of the film and improves the absorption of agomelatine through buccal mucosa.

The film-forming materials useful in the backing layer include one or more materials selected from the group of: hypromellose (HPMC), hypromellose acetate succinate (HPMCAS), cellulose acetate phthalate (CAP), hydroxyethyl cellulose (HEC), polyvinyl alcohol (PVA), hypromellose phthalate (HPMCP), and polyvinyl alcohol phthalate (PVAP). These film-forming materials provide a good barrier effect on agomelatine, and effectively prevent agomelatine from diffusing out of the mucoadhesive layer into the oral cavity. The amount of film-forming materials in the backing layer is about 60-100% w/w, preferably 70-100% w/w or 80-100% w/w. The backing film formed has a good flexibility.

When the thickness of the backing layer is ≥10 µm and ≤60 µm, the irritation of the drug is significantly reduced. When the thickness of the backing layer is <10 µm, the irritation masking effect is not good. When the thickness of the backing layer is >60 µm, the release rate of the drug is affected. The preferred thickness of the backing layer is 10-60 µm. More preferred thickness is 10-40 µm.

In one embodiment, one or more flavoring agents can be independently added to the drug layer and/or the backing layer to mask the taste of agomelatine. Flavoring agents suitable for the drug layer and backing layer include, but are not limited to, sucrose, glucose, sodium saccharin, fructose, xylitol, stevia, aspartame, sucralose, neotame, acesulfame, peppermint oil, menthol, orange flavor, pineapple flavor, cherry flavor, apple flavor essence, banana flavor essence, blueberry flavor essence, peach flavor essence, mango flavor essence, and grape flavor essence. The amount of a flavoring agent in the composition is about 0.01-5%, preferably about 0.05-2% (w/w) in the mucoadhesive layer, and 0-5% w/w in the backing layer. Flavoring agents added to the film improve the taste and provide a good mouth feel of the film, and may improve patient's compliance.

One or more coloring agents, which can be selected from the group consisting of FD&C colors, D&C colors, and combinations thereof, may be added into one or both layers of the film.

The present invention provides an agomelatine oral transmucosal film with improved bioavailability. After the drug dissolves in the oral mucosa, it can self-emulsify to form a microemulsion to promote the permeation and absorption of the drug. The film is a bilayer formulation; its backing layer prevents the direct diffusion of the drug into the oral cavity and reduces the irritating taste of the drug. The agomelatine film has a uniform appearance, uniform thickness, and uniform color, and has a good drug stability. The drug is administered through the oral mucosa, which avoids the first pass metabolism of the drug and improves the bioavailability of the drug.

The agomelatine oral transmucosal film is absorbed through the oral mucosa and enters the bloodstream, with rapid absorption. In pharmacokinetic studies carried out in beagle dogs, the Tmax of oral tablet is 0.75 h in beagle dogs and the Tmax of the present agomelatine oral transmucosal film is 0.33-0.5 h. The present agomelatine oral transmucosal film reduces Tmax and accelerates the onset action.

The present invention provides a method for preparing agomelatine oral transmucosal bilayer film. The method comprises the following steps: (a) mixing agomelatine or a pharmaceutical acceptable salt thereof, one or more first film-forming materials, one or more oil phase excipients, and one or more surfactants in a first solvent to prepare a mucoadhesive film solution; (b) coating the mucoadhesive film solution on a substrate and drying the mucoadhesive film solution to form the mucoadhesive layer; (c) mixing one or more second film-forming materials in a second solvent to prepare a backing film solution; (d) coating the backing film solution on the mucoadhesive layer and drying the backing film solution to form a bilayer film on the substrate; and (e) removing the bilayer film from the substrate to form the oral transmucosal agomelatine film.

In step (a) and (c), the first and the second solvent independently comprise 40-100% w/w of an organic solvent in water. The organic solvent is selected from the group consisting of: ethanol, isopropanol, acetone, t-butyl alcohol, dichloromethane, and any combination thereof. Preferable organic solvents include ethanol or isopropanol. The solvents allow all the materials to dissolve completely and form a homogeneous solution. Using a mixture of an organic solvent and water during preparation of the film results in agomelatine in an amorphous form in the film.

In steps (a) and (c), a flavoring agent and/or a coloring agent is optionally added in the solution to improve the flavor and color.

In step (b) and (d), the drying temperature is about 40°-100° C., preferably about 60-90° C.

By the present process, agomelatine is in an amorphous form in the mucoadhesive layer so that the film can produce a fast dissolution rate and improve the bioavailability of agomelatine.

The substrate that the bilayer film formed on includes polyethylene terephthalate, polypropylene resins, and polymethylpentene resins.

After step (e), the bilayer film is optionally cut into a suitable size and shape, and then further wrapped or packaged.

The agomelatine oral transmucosal film or patch of the present invention has a length of about 1-4 cm, and a width about 1-4 cm; preferably a length of about 1-3 cm, and width about 1-3 cm.

The present invention also provides a method for administering agomelatine to a subject. The method comprises identifying a subject in need thereof, and administering to the buccal mucosa or sublingual mucosa of the subject the transmucosal film of the present invention. The method is suitable to treat depression, insomnia and some psychic diseases.

The present film is useful in treating a subject that is a mammal, such as humans, horses, dogs, and cats. The present invention is particularly useful in treating humans.

The following examples further illustrate the present invention. These examples are intended merely to be illustrative of the present invention and are not to be construed as being limiting.

EXAMPLES

Example 1: Agomelatine Film (Crystalline Film)

In this example, Agomelatine films were prepared according to the formulation and process below.

| Formula: | |
|---|---|
| Agomelatine (crystalline) | 1.00 mg (5.0% w/w) |
| Hypromellose | 16.0 mg (80.0% w/w) |
| Hydroxypropyl Cellulose | 2.58 mg (12.9% w/w) |
| Sucralose | 0.40 mg (2.0% w/w) |
| FD&C Yellow No. 6 | 0.02 mg (0.1% w/w) |
| Purified water | 105.0 mg (Removed during the process of drying) |

Manufacturing Process:

Dissolve/disperse the Agomelatine into solvent with continuous stirring,

Add other excipients and continue stirring until the excipients completely dissolves Apply vacuum or stand aside to remove the bubbles, Coat the defoamed film solution in uniform thickness on a substrate, Dry the coating at temperature of about 60° C. to 90° C. to form a film on the conveyor belt, After the film was formed, cut the film into a suitable size, shape and packed in to pouch or in a suitable container.

Agomelatine film prepared according to the above formula and process had good film property, was easy to tear off from the substrate, had a smooth appearance and uniform in color, and the active ingredient Agomelatine crystalline powder particles were evenly coated on the film. X-ray powder diffraction study shows that agomelatine is in a crystalline state. In the dissolution test, after the drug film was dissolved, the drug particles were released and suspended in the dissolution medium, and the dissolution was slow and incomplete.

TABLE 1

| Dissolution Test Result of Example 1 | | | | | | | |
|---|---|---|---|---|---|---|---|
| Media | pH 6.8 Phosphate Buffer | | | | | | |
| Time (min) | 5 | 10 | 15 | 20 | 30 | 45 | 60 |
| Dissolved (%) | 14 | 24 | 34 | 45 | 57 | 61 | 63 |

The Agomelatine film prepared in was compared with Agomelatine tablet, and the pharmacokinetics study was conducted in beagle dogs. The results showed that the bioavailability of Agomelatine film was 2.2 times higher than that of the tablet. See Example 10 for the experimental results.

At the same time, different concentrations of ethanol solution (0-30%) and isopropanol solution (0-30%) were used to replace water in the formula and tested. The XRD study of these prepared films shows the API was in a crystalline form and the dissolution was slow.

Example 2: Agomelatine Film (Amorphous Film)

In this example, 50% ethanol solution used as preparation solvent instead of purified water, the other formulation excipients and manufacturing process is same as described in Example 1. Agomelatine used in this formulation is in the same crystalline form as used in Example 1.

| Formulation: | |
|---|---|
| Agomelatine (crystalline) | 1.00 mg (5.0% w/w) |
| Hypromellose | 16.0 mg (80.0% w/w) |
| Hydroxypropyl Cellulose | 2.58 mg (12.9% w/w) |
| Sucralose | 0.40 mg (2.0% w/w) |
| FD&C Yellow No. 6 | 0.02 mg (0.1% w/w) |
| 50% ethanol | 105.0 mg (Removed during the process of drying) |

The Agomelatine film prepared had smooth appearance, uniform color, and no visible crystalline particles seen on the film. The X-ray powder diffraction study of the agomelatine film showed that agomelatine was in an amorphous state. The dissolution experiment showed that 95% of drug dissolved in 10 minutes, but then dropped to 76% due to the supersaturation. Therefore, in terms of drug dispersion uniformity and dissolution, the amorphous agomelatine film prepared in Example 2 is superior to the crystalline film described in Example 1. However, the amorphous agomelatine film of Example 2 was easy to precipitate again due to its low solubility.

TABLE 2

Dissolution Test Result of example 2

| Media | pH 6.8 Phosphate Buffer | | | | | | |
|---|---|---|---|---|---|---|---|
| Time (min) | 5 | 10 | 15 | 20 | 30 | 45 | 60 |
| Dissolved (%) | 82 | 95 | 101 | 92 | 82 | 77 | 76 |

The Agomelatine film of Example 2 was used to in animal study and its bioavailability was 8.9 times of that of an oral tablet, which was significantly improved compared with the crystalline film of Example 1. See Example 10 for the experimental results.

Example 3: Agomelatine Film (Amorphous Film+Surfactant)

In this experiment, polysorbate 80 added as surfactant, the other formulation details are same as example 2. The manufacturing process is similar to example 1.

| Formulation: | |
|---|---|
| Agomelatine | 1.00 mg (5.0% w/w) |
| Hypromellose | 15.6 mg (78.0% w/w) |
| Hydroxypropyl Cellulose | 2.58 mg (12.9% w/w) |
| Polysorbate 80 | 0.40 mg (2.0% w/w) |
| Sucralose | 0.40 mg (2.0% w/w) |
| FD&C Yellow No. 6 | 0.02 mg (0.1% w/w) |
| 50% ethanol | 105.0 mg (Removed during the process of drying) |

The Agomelatine film prepared according to the above formula has smooth appearance, uniform color, and no visible crystalline particles seen on the film. The X-ray powder diffraction study of the agomelatine film shows that agomelatine is in an amorphous state. The dissolution experiment showed that 98% of drug dissolved in 10 minutes, and it maintained a fully dissolved state thereafter. Therefore, the prepared Agomelatine film containing surfactant (Example 3) avoided the problem of recrystallization of drug after dissolution (Example 2).

TABLE 3

Dissolution Test Result of example 3

| Media | pH 6.8 Phosphate Buffer | | | | |
|---|---|---|---|---|---|
| Time (min) | 5 | 10 | 15 | 20 | 30 |
| Dissolved (%) | 86 | 98 | 100 | 101 | 100 |

The Agomelatine film of Example 3 was used in animal study, and its bioavailability was 12.3 times of that of the oral tablet, which was significantly improved compared with the amorphous film without surfactant in Example 2. See Example 10 for the experimental results.

At the same time, 40-100% of different aqueous solutions such as ethanol aqueous solution, isopropanol aqueous solution, dichloromethane aqueous solution, acetone aqueous solution, and tert-butyl alcohol aqueous solution, as well as different film forming materials, such as hypromellose, hydroxypropyl cellulose, ethylene glycol and vinyl ethanol graft copolymer, polyvinyl alcohol, copovidone, polyethylene oxide were used to prepare agomelatine films and evaluated. In all the trials, agomelatine retained its amorphous form in the films, with uniform appearance, fast dissolution and no recrystallization or precipitation after dissolution.

Example 4: Agomelatine Film (Amorphous Film+Surfactant+Oil Phase Excipient)

In this experiment, medium-chain triglycerides (Labrafac™ lipophile WL 1349, Gattefosse company) in the oil phase excipient was added, the other formulation details are same as example 3. The manufacturing process is similar to example 1.

| Formulation: | |
|---|---|
| Agomelatine | 1.00 mg (5.0% w/w) |
| Hypromellose | 15.2 mg (76.0% w/w) |
| Hydroxypropyl Cellulose | 2.58 mg (12.9% w/w) |
| Polysorbate 80 | 0.40 mg (2.0% w/w) |
| Medium Chain Triglycerides | 0.40 mg (2.0% w/w) |
| Sucralose | 0.40 mg (2.0% w/w) |
| FD&C Yellow No. 6 | 0.02 mg (0.1% w/w) |
| 50% ethanol | 105.0 mg (Removed during the process of drying) |

The dissolution experiment showed that 97% of drug dissolved in 10 minutes, and it can be maintained in a fully dissolved state thereafter, but the emulsification state was not successfully formed. The Agomelatine film of Example 4 was used in animal study, and its bioavailability was 11.7 times that of the oral tablet, which was similar to the amorphous film in Example 3. See Example 10 for the experimental results.

Example 5: Agomelatine Film (Amorphous Film+Surfactant+Oil Phase Excipient, Self-Emulsifying)

In this experiment, the surfactant was replaced with lauroyl Polyoxyl-32 glycerides and the oil phase excipient was replaced with diethylene glycol monoethyl ether, the other formulation details are same as Example 4. The manufacturing process is similar to example 1.

| Formulation | |
|---|---|
| Agomelatine | 1.00 mg (5.0% w/w) |
| Hypromellose | 15.2 mg (76.0% w/w) |
| Hydroxypropyl Cellulose | 2.58 mg (12.9% w/w) |
| Lauroyl Polyoxyl-32 glycerides | 0.40 mg (2.0% w/w) |
| Diethylene glycol Monoethyl ether, | 0.40 mg (2.0% w/w) |
| Sucralose | 0.40 mg (2.0% w/w) |
| FD&C Yellow No. 6 | 0.02 mg (0.1% w/w) |
| 50% ethanol | 105.0 mg (Removed during the process of drying) |

The dissolution experiment showed that 94% of drug dissolved in 10 minutes, and it maintained in a fully dissolved state thereafter, and formed a micro-emulsion self-emulsified state after disintegration. The Agomelatine film of Example 5 was used in animal study, and its bioavailability was 46.7 times that of the oral tablet, which was significantly improved compared with the amorphous film containing surfactant in Example 3. See Example 10 for the experimental results.

Example 6: Agomelatine Film (Amorphous Film+Surfactant+Oil Phase Excipient)

In these examples, different oil phase excipients were tested; the other formulation details are same as example 5. The manufacturing process is similar to example 1. The formulation details are given below.

Dissolution experiments of agomelatine film prepared according to the above formulations were performed. The results showed that drugs in Examples 6-1 and 6-2 were dissolved after the dissolution of the drug films, but an emulsification state was not formed. Drugs in Examples 6-3 and 6-4 were dissolved after the dissolution of the drug films, and the emulsification state of microemulsion was successfully formed.

In all Examples 6-1 to 6-4, the agomelatine retains its amorphous form.

In similar experiments, other oil phase excipients such as medium chain triglyceride, span 80, polyoxyethylene 35 castor oil, monoglyceride of oleic acid, diethylene glycol monoethyl ether, oleoyl polyoxyl-6 glycerides were tested. The results showed that agomelatine films prepared by using medium chain triglyceride, span 80, polyoxyethylene 35 castor oil as the oil phase excipient did not self-emulsify. The results also showed that agomelatine films prepared using monoglyceride of oleic acid, diethylene glycol monoethyl ether, and oleoyl polyoxyl-6 glycerides as the oil phase excipient self-emulsified.

Different concentrations of oil phase excipients such as 1%, 5%, 10%, 15%, 20%, and 30% were tested. When the oil phase excipient concentration was between 1-20%, the film had acceptable properties after drying, and could self-emulsify. When the oil phase excipient concentration was 30%, the film after coating and drying was soft and easy to stick. The results showed that preferred concentration of oil phase excipient is 1-15%.

Example 7: Agomelatine Film (Amorphous Film+Surfactant+Oil Phase Excipient)

In these examples, different surfactants (emulsifiers) were evaluated; other formulation details were the same as example 5. The manufacturing process was similar to example 1. The formulation details are given below.

| Composition | 6-1 | 6-2 | 6-3 | 6-4 |
|---|---|---|---|---|
| Agomelatine | 1.00 mg (5.0% w/w) | 1.00 mg (5.0% w/w) | 0.10 mg (0.5% w/w) | 5.00 mg (25.0% w/w) |
| Hypromellose | 17.18 mg (85.9% w/w) | 17.18 mg (85.9% w/w) | 19.28 mg (96.4% w/w) | 9.58 mg (47.9% w/w) |
| Lauroyl Polyoxyl-32 glycerides | 0.40 mg (2.0% w/w) | 0.40 mg (2.0% w/w) | 0.20 mg (1.0% w/w) | 3.00 mg (15.0% w/w) |
| Polyoxyethylene 40 hydrogenated Castor oil | 1.00 mg (5.0% w/w) | — | — | — |
| Sorbitan monolaurate 20 | — | 1.00 mg (5.0% w/w) | — | — |
| Propylene glycol dicaprate | — | — | 0.20 mg (1.0% w/w) | — |
| Glyceryl monolinoleate | — | — | — | 2.00 mg (10.0% w/w) |
| Sucralose | 0.40 mg (2.0% w/w) | 0.40 mg (2.0% w/w) | 0.20 mg (1.0% w/w) | 0.40 mg (2.0% w/w) |
| FD&C Yellow No. 6 | 0.02 mg (0.1% w/w) | 0.02 mg (0.1% w/w) | 0.02 mg (0.1% w/w) | 0.02 mg (0.1% w/w) |
| 40% ethanol | — | — | 105.0 mg | — |
| 50% ethanol | 105.0 mg | 105.0 mg | — | — |
| 100% ethanol | — | — | — | 105.0 mg |

Note:
The solvents used in the manufacturing process removed during the process of drying.

| Composition | 7-1 | 7-2 | 7-3 | 7-4 |
|---|---|---|---|---|
| Agomelatine | 1.00 mg (5.0% w/w) | 1.00 mg (5.0% w/w) | 1.00 mg (5.0% w/w) | 1.00 mg (5.0% w/w) |
| Hypromellose | 14.6 mg (73.0% w/w) | 14.6 mg (73.0% w/w) | 14.6 mg (73.0% w/w) | 14.6 mg (73.0% w/w) |
| Hydroxypropyl cellulose | 2.58 mg (12.9% w/w) | 2.58 mg (12.9% w/w) | 2.58 mg (12.9% w/w) | 2.58 mg (12.9% w/w) |
| Polysorbate 80 | 1.00 mg (5.0% w/w) | — | — | — |
| Poloxamer | — | 1.00 mg (5.0% w/w) | — | — |
| Stearic acid polyethylene glycol glycerol ester | — | — | 1.00 mg (5.0% w/w) | — |
| Lauroyl Polyoxyl-32 glycerides | — | — | — | 1.00 mg (5.0% w/w) |
| Diethylene glycol monoethyl ether | 0.40 mg (2.0% w/w) | 0.40 mg (2.0% w/w) | 0.40 mg (2.0% w/w) | 0.40 mg (2.0% w/w) |
| Sucralose | 0.40 mg (2.0% w/w) | 0.40 mg (2.0% w/w) | 0.40 mg ((2.0% w/w) | 0.40 mg (2.0% w/w) |
| FD&C Yellow No. 6 | 0.02 mg (0.1% w/w) | 0.02 mg (0.1% w/w) | 0.02 mg (0.1% w/w) | 0.02 mg (0.1% w/w) |
| 50% ethanol | 105.0 mg | 105.0 mg | 105.0 mg | 105.0 mg |

Note:
The solvents used in the manufacturing process removed during the process of drying.

Dissolution experiments were performed. The results of Examples 7-1 and 7-2 showed that the drug was dissolved after film was disintegrated but emulsification state was not formed. The results of Examples 7-3 and 7-4 showed that the drug was dissolved after film disintegrated, and the emulsification state of microemulsion was successfully formed after the disintegration.

Other surfactants (emulsifiers) such as Tween 20, stearic acid, glycerol monostearate, oleic acid polyethylene glycol glyceride, linoleoyl polyoxyl-6 glycerides, and sodium dodecyl sulfate were also tested. Agomelatine films prepared using tween 20, stearic acid, glycerol monostearate did not self-emulsify. Agomelatine films prepared using oleic acid polyethylene glycol glyceride, linoleoyl Polyoxyl-6 glycerides, sodium dodecyl sulfate as surfactant (emulsifier) realized self-emulsification.

Different concentrations of surfactants such as 1%, 5%, 10%, 15% and 20% were also tested. When the concentration of surfactant was 1-15%, agomelatine film had a good appearance after coating and drying process, and it could self-emulsify. When the surfactant concentration was 20%, self-emulsification could not be formed. The results showed that preferred concentration of surfactants (emulsifiers) was 1-10%.

Example 8: Agomelatine Film Agent (Single Film Taste)

In this embodiment, the sample obtained from Example 5 (single layer self-emulsifying film) was subjected to taste testing on multiple volunteers. When the film was applied to the oral mucosa, the film began to dissolve, the drug was released, and the volunteers said that the drug had a significant tongue irritation and poor taste.

In the experiment, a single layer film was used to test different kinds of flavoring agents (Menthol, orange flavor essence, cherry flavor essence, apple flavor essence, etc.), different combinations of sweeteners (sucrose, glucose, saccharin sodium, fructose, Xylitol, *stevia*, Aspartame, Sucralose, etc.), and different combinations of sweeteners and flavoring agents were also used to mask the taste (such as sucralose and menthol, Xylitol and menthol, etc.). After testing, it was found that none of them significantly improved the irritation of agomelatine to the tongue.

Example 9. Agomelatine Film (Bilayer Film)

In this example a backing layer is added on the base layer of the Example 5. The formulation details of the bilayer film are shows as follows,

| Example 9 | | |
|---|---|---|
| Drug layer | Agomelatine | 1.00 mg (5.0% w/w) |
| | Hypromellose | 17.78 mg (88.9% w/w) |
| | Lauroyl Polyoxyl-32 glycerides (Surfactant) | 0.40 mg (2.0% w/w) |
| | Diethylene glycol Monoethyl ether (Oil) | 0.40 mg (2.0% w/w) |
| | Sucralose | 0.40 mg (2.0% w/w) |
| | FD&C Yellow No. 6 | 0.02 mg (0.1% w/w) |
| | 50% ethanol | 105.00 mg |
| Backing layer | Hypromellose | 12.75 mg (85.0% w/w) |
| | Menthol | 0.30 mg (2.0% w/w) |
| | Sucralose | 0.45 mg (3.0% w/w) |
| | Titanium dioxide | 1.50 mg (10.0% w/w) |
| | 50% Ethanol | 85.00 mg |

Note:
The solvents used in the manufacturing process removed during the process of drying.

Manufacturing Process:

Drug layer: Dissolve Agomelatine into solvent with continuous stirring, add other excipients and continue stirring until all the excipients completely dissolves, apply vacuum or stand aside to remove the bubbles. Coat the defoamed film solution in uniform thickness on a substrate; dry the coating at temperature of about 60° C. to 90° C. to form a film on the conveyor belt.

Backing layer: Add all excipients except titanium dioxide into solvent and continuous stirring until all the excipients completely dissolves, then add titanium dioxide stir and disperse uniformly. Apply vacuum or stand aside to remove the bubbles. Coat the defoamed film solution in uniform thickness on to the dried drug layer. Dry the coating at temperature of about 60° C. to 90° C. to form a bilayer film on the conveyor belt. After the film is formed, cut the film into a suitable size, shape and packed in to pouch or in a suitable container.

Agomelatine film prepared in Example 9 had good film property, smooth appearance, uniform color, white backing layer and orange adhesive drug layer.

The samples obtained from the Example 9 were subjected to taste evaluation on multiple volunteers, and the volunteers reported that no tongue irritation was felt throughout the administration process, which a significant improvement in taste compared to the single-layer film of Example 8. The pharmacokinetic experiment of Agomelatine film of Example 9 showed that its bioavailability was 51.7 times that of oral tablet. See Example 10 for the experimental results.

In addition, other different types of backing film forming materials such as povidone (PVP), ethylene glycol and vinyl ethanol graft copolymer (PVA-PEG), hydroxypropyl cellulose (HPC), polyethylene oxide (PEO), hypromellose (HPMC), cellulose acetate phthalate (CAP), hydroxyethyl cellulose (HEC), polyvinyl alcohol (PVA), hypromellose phthalate (HPMCP), hypromellose acetate succinate (HPMCAS), polyvinyl alcohol pthalate (PVAP) at different concentration of 50-100% (w/w) and at different thickness of backing layer (5 μM~100 μm) were tested. The results shows that formulations using PVP, polyvinyl alcohol polyethylene glycol copolymer (PVA-PEG), hydroxypropyl cellulose (HPC), and polyethylene oxide (PEO) did not improve the taste of the formulation. The use of hypromellose acetate succinate (HPMCAS), Hypromellose (HPMC), Cellulose acetate phthalate (CAP), hydroxyethyl cellulose (HEC), polyvinyl alcohol (PVA), Hypromellose Phthalate (HPMCP), polyvinyl pthalate (PVAP) in concentration of 80-100% (w/w) significantly improved the taste of the drug film. When the thickness of the backing layer is ≥10 μm and ≤60 μm, the irritation of the drug is significantly reduced. When the thickness of the backing layer is <10 μm, the irritation masking effect is not good. When the thickness of the backing layer is >60 μm, the release rate of the drug is affected. The preferred thickness of the backing layer is 10-60 μm. More preferred thickness is 10-40 μm.

At the same time, sweeteners and flavoring agents were added to the backing layer prescription to further improve the taste of the formulation. Sweeteners and flavoring agents such as sucralose, aspartame, saccharin sodium, neotame, acesulfame, menthol, peppermint oil, orange flavor essence, pineapple flavor essence, cherry flavor essence, blueberry flavor essence and grape flavor essence, with the concentration ranging from 0.01% to 5% w/w, were tested. The results show that all tested sweeteners and flavoring agents improved the taste of the formulation.

Example 10: Bioavailability Study of Agomelatine Film

In this example, Pharmacokinetic parameters were tested and compared between oral tablet and buccal films of this application. Agomelatine oral tablet 25 mg RLD (Valdoxan) and agomelatine buccal films 1 mg of Examples 1, 2, 3, 4, 5, and 9 were tested on beagle dogs. In the agomelatine film group, films containing 1 mg of agomelatine were administered on to the buccal mucosa. In the tablet group, Agomelatine RLD tablets (25 mg) were administered orally with water. Blood samples were withdrawn before administration (0 min) and 0.17 h, 0.33 h, 0.5 h, 0.75 h, 1.0 h, 1.5 h, 2.0 h, 3.0 h, 4.0 h, 5.0 h, 6.0 h after administration. The concentration of agomelatine in blood was determined by LC-MS/MS method, and the relative bioavailability of the agomelatine film and RLD tablets was calculated. The results are shown in the following Table 4. The relative bioavailability of the buccal film in Examples 1-5 and 9 were 221%, 892%, 1233%, 1167%, 4674%, and 5167% respectively. The Tmax values were 0.75 h, 0.5 h, 0.5 h, 0.5 h, 0.33 h, and 0.39 h, which were significantly lower than the Tmax values of the oral tablets. The results showed that the buccal mucosa film of the present invention had a significantly faster absorption rate and higher bioavailability than that of an oral tablet. A comparison between Examples 1 and 2 reveals that the bioavailability of the film with amorphous agomelatine (Example 2) was higher than that of crystalline agomelatine. The results indicate that agomelatine in an amorphous form in the prepared film had a better bioavailability than agomelatine in a crystalline form. Comparison between results of Example 2 and Example 3 reveals that the addition of surfactants to an amorphous agomelatine film can improve the bioavailability. Result comparison of Examples 3-5 reveals that by adding oil phase excipient to Example 3, if self-emulsification was not formed (Example 4), then there was no significant difference in bioavailability; however, if the formulation self-emulsified (Example 5), the bioavailability was significantly higher than that of a formulation without self-emulsification. There was no significant difference in bioavailability between Example 5 and Example 9, but the bi-layer film showed significant improvement in taste.

TABLE 8

Bioavailability Test results

| | Tablet | Example 1 | Example 2 | Example 3 | Example 4 | Example 5 | Example 9 |
|---|---|---|---|---|---|---|---|
| Dose | 25 mg | 1 mg | 1 mg | 1 mg | 1 mg | 1 mg | 1 mg |
| Formulation characteristics | N/A | Crystal film | Amorph film | Amorph film | Amorph film | Amorph film | Amorph film |
| | | N/A | N/A | Adding surfactant | Adding surfactant/ emulsifier | Adding surfactant/ emulsifier | Adding surfactant/ emulsifier |
| | | N/A | N/A | N/A | No Self-emulsification | Self-emulsification seen | Self-emulsification seen |
| | | Single layer film | Single layer film | Single layer film | Single layer film | Single layer film | Bi layer film |
| Pharmacokinetic | | | | | | | |
| Mean T$_{max}$ (h) | 0.75 | 0.75 | 0.5 | 0.5 | 0.5 | 0.0.33 | 0.39 |

TABLE 8-continued

Bioavailability Test results

| | Group | | | | | | |
|---|---|---|---|---|---|---|---|
| | Tablet | Example 1 | Example 2 | Example 3 | Example 4 | Example 5 | Example 9 |
| | | | | | Dose | | |
| | 25 mg | 1 mg | 1 mg | 1 mg | 1 mg | 1 mg | 1 mg |
| Mean AUC$_{0-6h}$ (hr*ng/mL) | 128.7 | 11.4 | 45.9 | 63.5 | 60.1 | 240.6 | 266.0 |
| Relative bioavailability (%)* | 100% | 221% | 892% | 1233% | 1167% | 4674% | 5167% |
| Taste | N/A | Strong Irritability | Strong Irritability | Strong Irritability | Strong Irritability | Strong Irritability | No irritation |

*Relative Bioavailability = $\frac{AUC_{film}}{AUC_{tablet}} \times \frac{Dose_{tablet}}{Dose_{film}} = \frac{AUC_{film}}{AUC_{tablet}} \times \frac{25 \text{ mg}_{tablet}}{1 \text{ mg}_{film}}$ The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. An oral transmucosal film, comprising:
   (a) a mucoadhesive layer comprising 0.1%-40% by weight of amorphous agomelatine or a pharmaceutical acceptable salt thereof, 50%-98% by weight of a first film-forming material, 1%-5% by weight of an oil phase excipient, and 1%-5% by weight of a surfactant; and
   (b) a water-soluble backing layer comprising 60%-100% by weight of a second film-forming material, wherein the backing layer prevents agomelatine from diffusing into the oral cavity of a patient during oral administration of the film;
   wherein the first film-forming material comprises one or more materials selected from the group consisting of: hypromellose (HPMC), hydroxypropyl cellulose (HPC), ethylene glycol and vinyl ethanol graft copolymer, polyvinyl alcohol (PVA), copovidone (PVP), and polyethylene oxide (PEO), and
   the second film-forming material comprises one or more materials selected from the group consisting of: hypromellose, hypromellose acetate succinate, cellulose acetate phthalate, hydroxyethyl cellulose, polyvinyl alcohol, hypromellose phthalate, and polyvinyl alcohol phthalate; and
   wherein the oil phase excipient is glyceryl monolinoleate and the surfactant is sodium dodecyl sulfate, the oil phase excipient is diethylene glycol monoethyl ether and the surfactant is sodium dodecyl sulfate, the oil phase excipient is glyceryl monolinoleate and the surfactant is linoleoyl polyoxyl-6 glyceride, or the oil phase excipient is propylene glycol monolaurate and the surfactant is polyoxyl 15 hydroxystearate.

2. The film according to claim 1, wherein the thickness of the backing layer is 10 µm-60 µm.

3. The film according to claim 1, wherein the mucoadhesive layer comprises 0.5%-25% by weight of amorphous agomelatine.

4. The film according to claim 1, wherein the mucoadhesive layer further contains one or more flavoring agents and/or one or more sweeteners.

5. The film according to claim 1, wherein the backing layer further contains one or more flavoring agents and/or one or more sweeteners.

6. The film according to claim 1, wherein the mucoadhesive layer comprises 0.5%-25% by weight of amorphous agomelatine or the pharmaceutical acceptable salt thereof, and 70%-95% by weight of the first film-forming material.

7. The film according to claim 3, wherein the mucoadhesive layer comprises 0.5%-25% by weight of amorphous agomelatine or the pharmaceutical acceptable salt thereof, and 70%-95% by weight of the first film-forming material.

8. The film according to claim 7, wherein the mucoadhesive layer comprises 0.1 mg-10 mg of amorphous agomelatine.

9. The film according to claim 1, wherein the mucoadhesive layer further contains an adhesive to improve the adhesion of the film to the oral mucosa.

10. A process for preparing the oral transmucosal film according to claim 1, comprising the steps of:
   (a) mixing agomelatine or a pharmaceutical acceptable salt thereof, the first film-forming material, the oil phase excipient, and the surfactant in a first solvent to prepare a mucoadhesive film solution;
   (b) coating the mucoadhesive film solution on a substrate and drying the mucoadhesive film solution to form the mucoadhesive layer;
   (c) mixing the second film-forming material in a second solvent to prepare a backing film solution;
   (d) coating the backing film solution on the mucoadhesive layer and drying the backing film solution to form a bilayer film on the substrate; and
   (e) removing the bilayer film from the substrate to form the oral transmucosal agomelatine film,
   wherein the first solvent and the second solvent independently comprise 40%-100% w/w of an organic solvent in water, wherein the organic solvent is selected from the group consisting of: ethanol, isopropanol, acetone, t-butyl alcohol, dichloromethane, and any combination thereof; and wherein the oral transmucosal film comprises:
(a) the mucoadhesive layer comprising 0.1%-40% by weight of amorphous agomelatine or a pharmaceutical acceptable salt thereof, 50%-98% by weight of the first film-forming material, 1%-5% by weight of the oil phase excipient, and 1%-5% by weight of the surfactant; and
(b) the water-soluble backing layer comprising 60%-100% by weight of the second film-forming material, wherein the backing layer prevents agomelatine from diffusing into the oral cavity of a patient during oral administration of the film;

wherein the first film-forming material comprises one or more materials selected from the group consisting of: hypromellose (HPMC), hydroxypropyl cellulose (HPC), ethylene glycol and vinyl ethanol graft copolymer, polyvinyl alcohol (PVA), copovidone (PVP), and polyethylene oxide (PEO), and the second film-forming material comprises one or more materials selected from the group consisting of: hypromellose, hypromellose acetate succinate, cellulose acetate phthalate, hydroxyethyl cellulose, polyvinyl alcohol, hypromellose phthalate, and polyvinyl alcohol phthalate; and wherein the oil phase excipient is glyceryl monolinoleate and the surfactant is sodium dodecyl sulfate, the oil phase excipient is diethylene glycol monoethyl ether and the surfactant is sodium dodecyl sulfate, the oil phase excipient is glyceryl monolinoleate and the surfactant is linoleoyl polyoxyl-6 glyceride, or the oil phase excipient is propylene glycol monolaurate and the surfactant is polyoxyl 15 hydroxystearate.

11. The method of claim 10, wherein the organic solvent is ethanol.

* * * * *